(12) United States Patent
Abe et al.

(10) Patent No.: US 9,085,645 B2
(45) Date of Patent: Jul. 21, 2015

(54) SUGAR CHAIN FLUORESCENT LABELING METHOD

(75) Inventors: Midori Abe, Tokyo (JP); Hideyuki Shimaoka, Tokyo (JP)

(73) Assignee: SUMITOMO BAKELITE CO., LTD., Tokyo (JP)

(*) Notice: Subject to any disclaimer, the term of this patent is extended or adjusted under 35 U.S.C. 154(b) by 0 days.

(21) Appl. No.: 13/980,795

(22) PCT Filed: Mar. 8, 2012

(86) PCT No.: PCT/JP2012/056011
§ 371 (c)(1),
(2), (4) Date: Jul. 19, 2013

(87) PCT Pub. No.: WO2012/124609
PCT Pub. Date: Sep. 20, 2012

(65) Prior Publication Data
US 2013/0310552 A1 Nov. 21, 2013

(30) Foreign Application Priority Data
Mar. 11, 2011 (JP) ................................. 2011-053897

(51) Int. Cl.
*G01N 21/64* (2006.01)
*G01N 33/66* (2006.01)
*C08B 37/00* (2006.01)
*G01N 33/533* (2006.01)
*C09K 11/06* (2006.01)
*G01N 30/88* (2006.01)

(52) U.S. Cl.
CPC .................. *C08B 37/00* (2013.01); *C09K 11/06* (2013.01); *G01N 21/643* (2013.01); *G01N 33/533* (2013.01); *C09K 2211/1433* (2013.01); *G01N 2030/8827* (2013.01)

(58) Field of Classification Search
CPC ........... C08B 37/00; G01N 2030/8836; G01N 21/64; G01N 21/6428; G01N 21/643; G01N 21/6486; G01N 33/48; G01N 33/66; G01N 2030/8827; G01N 2030/8831; G01N 33/533; C09K 11/06; C09K 2211/1433
USPC ......... 436/63, 71, 87, 94, 106, 111, 127, 128, 436/140, 164, 172, 174, 177, 178; 422/430, 422/68.1, 82.05, 82.08; 536/123.1
See application file for complete search history.

(56) References Cited

U.S. PATENT DOCUMENTS

| 4,975,533 | A | 12/1990 | Kondo et al. | |
|---|---|---|---|---|
| 7,816,517 | B2 * | 10/2010 | Nakakita et al. | 536/124 |
| 2009/0306291 | A1 | 12/2009 | Shimaoka et al. | |
| 2011/0046364 | A1 * | 2/2011 | Abe et al. | 536/55.3 |
| 2011/0089033 | A1 * | 4/2011 | Shimaoka et al. | 204/451 |
| 2014/0099507 | A1 * | 4/2014 | Shimaoka et al. | 428/402 |

FOREIGN PATENT DOCUMENTS

| CN | 101501492 A | 8/2009 |
|---|---|---|
| EP | 0 867 722 A2 | 9/1998 |
| JP | 01 141356 | 6/1989 |
| JP | 07 20131 | 1/1995 |
| JP | 2005 241408 | 9/2005 |
| JP | 2006 098367 | 4/2006 |
| JP | 2007 212235 | 8/2007 |
| JP | 2008 309501 | 12/2008 |
| WO | 2008 018170 | 2/2008 |
| WO | 2009/133696 | * 11/2009 |

OTHER PUBLICATIONS

International Search Report Issued Apr. 3, 2012 in PCT/JP12/56011 Filed Mar. 8, 2012.
Office Action and Search Report issued on Aug. 5, 2014 in the corresponding Chinese Patent Application No. 201280009233.7 (with Search Report English Translation).
European Search Report dated Oct. 17, 2014, in European Patent Application No. 12757654.4.
Pabst M et al: "Comparison of fluorescent labels for oligosaccharides and introduction of a new postlabeling purification method", Analytical Biochemistry, Academic Press Inc, New York, vol. 384, No. 2, Jan. 15, 2009, pp. 263-273, XP026171981.
Petr Smejkal et al: "Chip-based CE for rapid separation of 8-aminopyrene-1,3,6-trisulfonic acid (APTS) derivatized glycans", Electrophoresis, vol. 31, No. 22, Oct. 22, 2010, pp. 3783-3786, XP055143985.
Lemoine Jerome et al: "Analysis of 8-aminonaphthalene-1,3,6-trisulfonic acid labelled N-glycans by matrix-assisted laser desorption/ionisation time-of-flight mass spectrometry", Rapid Communications in Mass Spectrometry, John Wiley & Sons, GB, vol. 14, No. 2, Jan. 1, 2000, pp. 100-104, XP002512791.
Bigge J C et al: "Nonselective and efficient fluorescent labelling of glycans using 2-amino benzamide and anthranilic acid", Analytical Biochemistry, Academic Press Inc, New York, vol. 230, No. 2, Jan. 1, 1995, pp. 229-238, XP002489980.
Xia Baoyun et al: "Versatile fluorescent derivatization of glycans for glycomic analysis", Nature Methods, Nature Publishing Group, GB, vol. 2, No. 11, Nov. 1, 2005, pp. 845-850, XP009093004.

* cited by examiner

*Primary Examiner* — Maureen Wallenhorst
(74) *Attorney, Agent, or Firm* — Oblon, McClelland, Maier & Neustadt, L.L.P.

(57) ABSTRACT

An object of the present invention is to provide a simple method for fluorescent labeling of sugar chains, and a sugar chain capturing carrier used therein. According to the present invention, a sugar chain fluorescent labeling method is provided in which sugar chains are captured, recovered and purified by primary amino groups in a sugar chain capturing carrier having the primary amino groups that is used to capture sugar chains, and the captured sugar chains are released from the carrier and then labeled with a fluorescent substance including aromatic amine at a concentration of 0.5 mol/L or more.

14 Claims, 2 Drawing Sheets

SUGAR CHAIN FLUORESCENT LABELING METHOD

TECHNICAL FIELD

The present invention relates to a method for fluorescent labeling of sugar chains comprising recovery, isolation, purification of sugar chain molecules and fluorescent labeling for measurement, and a sugar chain capturing carrier that captures sugar chain molecules.

The present application claims priority on the basis of Japanese Patent Application No. 2011-053897, filed in Japan on Mar. 11, 2011, the contents of which are incorporated herein by reference.

BACKGROUND ART

In the field of biochemistry, sugar chain molecules have recently attracted attention as the third major type of chain after nucleic acids and proteins. In particular, research has been conducted on their involvement in such processes as cell differentiation and malignant transformation, immune reactions and fertilization, and efforts are continuing to be made to develop these molecules into novel pharmaceuticals and medical materials.

In addition, since sugar chains are receptors for numerous toxins, viruses, bacteria and the like and are also attracting attention for use as cancer markers, similar efforts are continuing to be made in these fields as well in order to develop novel pharmaceuticals and medical materials.

However, although the importance of sugar chain research is recognized, due to their complex structure and diversity, research is progressing quite slowly in comparison with the first two types of chains in the form of nucleic acids and proteins.

Consequently, the need has arisen in recent years for methods capable of analyzing the structure of sugar chains rapidly, easily and with high accuracy, and sugar chains have been analyzed by various such methods, examples of which include high-performance liquid chromatography (HPLC), nuclear magnetic resonance, capillary electrophoresis (CE), mass spectrometry and lectin array-based analyses. In order to analyze sugar chains using these various techniques, it is necessary to first isolate and purify sugar chains from proteins, peptides, lipids and nucleic acids and the like contained in biological samples. In addition, although HPLC and CE are widely used from the viewpoints of quality of isolation, quality of reproducibility, quantitativity and high sensitivity, it is necessary to label the reducing terminal of a sugar chain by reductive amination and the like in order to obtain high sensitivity. However, these sugar chain purification and labeling procedures require both time and labor, and make it difficult to prepare a large number of samples at one time.

Various methods have been developed for analyzing sugar chains by fluorescent labeling (see, for example, Patent Documents 1, 2 and 3). However, since the labeling efficiency of these methods is not 100%, both labeled and unlabeled sugar chains are present in a single sample. Although this does not present a significant problem during fluorescence detection using HPLC or CE, there was the problem of peaks becoming excessively complex when analyzing sugar chains by mass spectrometry. In addition, in the case of poor labeling efficiency, there was also the possibility of the problem of decreased sensitivity even when analyzing by HPLC or CE.

PRIOR ART DOCUMENTS

Patent Documents

Patent Document 1: Japanese Unexamined Patent Application, First Publication No. H07-20131

Patent Document 2: Japanese Unexamined Patent Application, First Publication No. 2006-098367

Patent Document 3: Japanese Unexamined Patent Application, First Publication No. 2008-309501

DISCLOSURE OF THE INVENTION

Problems to be Solved by the Invention

An object of the present invention is to provide a simple and efficient method for fluorescent labeling of sugar chains.

Means for Solving the Problems

The aforementioned object is achieved by the present invention as described in (1) to (11) below.

(1) A sugar chain fluorescent labeling method, including: labeling a sugar chain by reacting a sugar chain with a fluorescent substance including an aromatic amine at a concentration of 0.5 mol/L or more.

(2) The sugar chain fluorescent labeling method described in (1), in which the aromatic ring moiety of the aromatic amine is a benzene ring, pyrene ring, naphthalene ring, acridone ring, fluorescein ring, dansyl ring, coumarine ring, acridine ring or derivative thereof.

(3) The sugar chain fluorescent labeling method described in (1) or (2), in which the excitation wavelength of the fluorescent substance including an aromatic amine is 330 nm to 750 nm.

(4) The sugar chain fluorescent labeling method described in any of (1) to (3), in which the emission wavelength of the fluorescent substance including an aromatic amine is 420 nm to 780 nm.

(5) The sugar chain fluorescent labeling method described in any of (1) to (4), in which the fluorescent substance having an aromatic amine is at least one type of fluorescent substance selected from 2-aminobenzamide, 2-aminobenzoic acid, 8-aminopyrene-1,3,6-trisulfonate, 8-aminonaphthalene-1,3,6-trisulfonate, 2-amino-9(1OH)-acridone, 5-aminofluorescein, dansyl ethylenediamine, 7-amino-4-methylcoumarine, 3-aminobenzoic acid, 7-amino-1-naphthol, 3-(acetylamino)-6-aminoacridine and derivatives of these fluorescent substances having an aromatic amine.

(6) The sugar chain fluorescent labeling method described in any of (1) to (5), in which after capturing and purifying a sugar chain using a sugar chain capturing carrier, the sugar chain is released from the sugar chain capturing carrier, and the free sugar chain is labeled with the fluorescent substance including an aromatic amine.

(7) The sugar chain fluorescent labeling method described in (6), in which the sugar chain capturing carrier is a polymer particle having a structure represented by the following Chemical Formula 1:

[Chemical Formula 1]

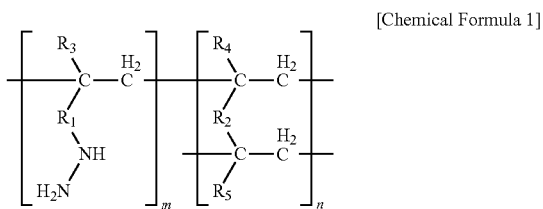

(in which, $R_1$ and $R_2$ represent hydrocarbon chains having 1 to 20 carbon atoms that may be inserted with —O—, —S—, —NH—, —CO— or —CONH—, $R_3$, $R_4$ and $R_5$ represent H, $CH_3$ or a hydrocarbon chain having 2 to 5 carbon atoms, and m and n represent the numbers of monomer units).

(8) The sugar chain fluorescent labeling method described in (6) or (7), in which the sugar chain capturing carrier is a polymer particle having a structure represented by the following Chemical Formula 2:

[Chemical Formula 2]

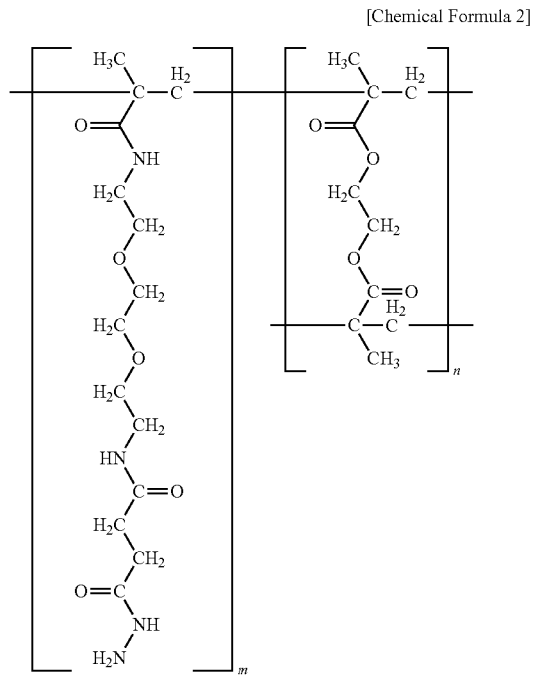

(in which, m and n are the same as previously defined).

(9) The sugar chain fluorescent labeling method described in any of (1) to (8), in which the sugar chain is a biological product.

(10) The sugar chain fluorescent labeling method described in any of (1) to (9), in which the sugar chain is a sugar chain bound to any of a glycoamino acid, glycopeptide, glycoprotein, glycolipid, glycosaminoglycan, proteoglycan, glycosylphosphatidylinositol, peptidoglycan or lipopolysaccharide, or a free sugar chain.

(11) A kit used in the sugar chain fluorescent labeling method described in any of (1) to (10).

Effects of the Invention

According to the present invention, sugar chain molecules can be fluorescent labeled both easily and efficiently.

BEST MODE FOR CARRYING OUT THE INVENTION

Figure 1:
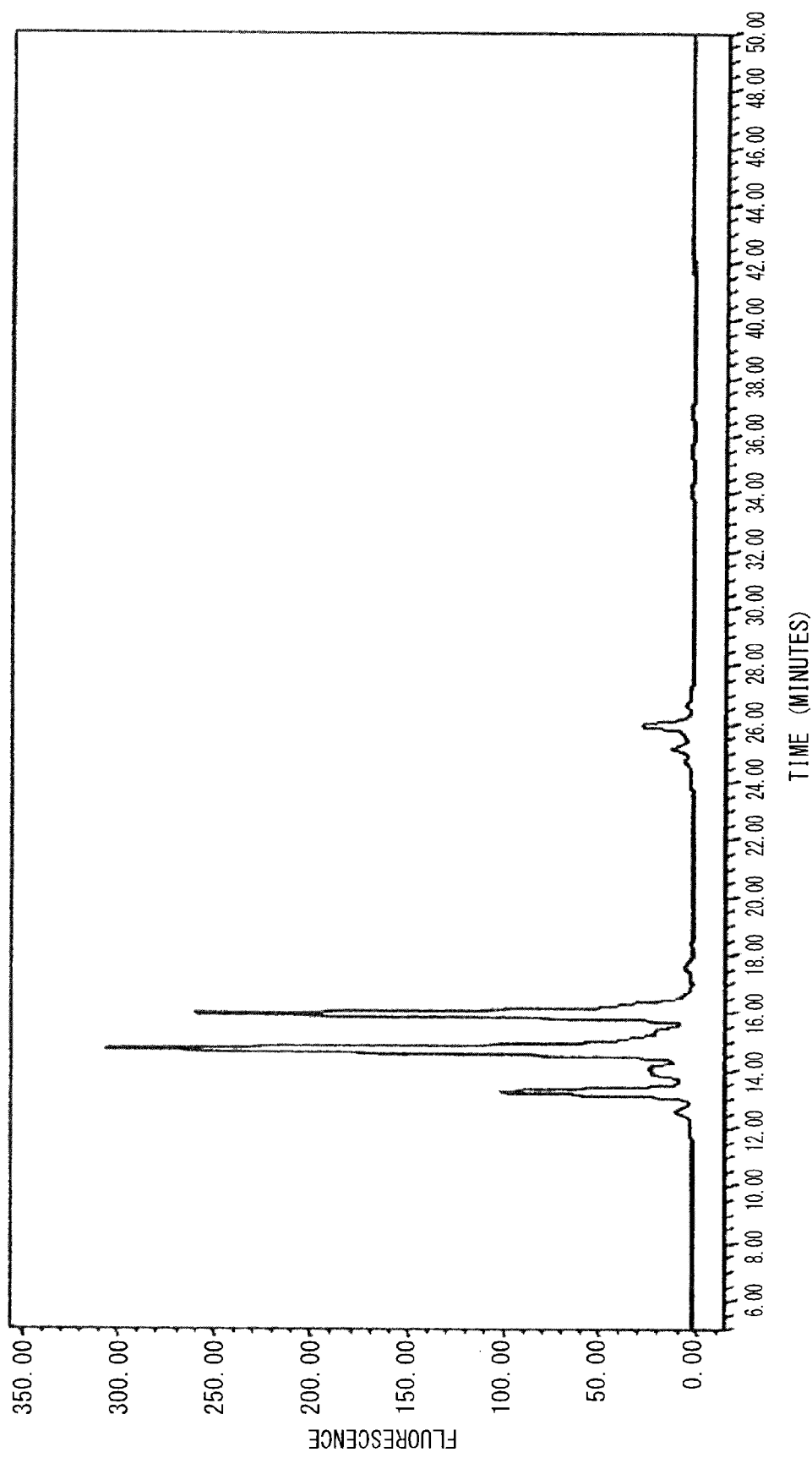
FIG. 1 is a typical example of an HPLC chart obtained in a study of an example of the present application.

The present invention relates to a sugar chain fluorescent labeling method for analyzing sugar chains by HPLC or mass spectrometry. In particular, the present invention relates to a method for capturing and purifying a sugar chain on a sugar chain capturing carrier followed by releasing the sugar chain and labeling the sugar chain with a fluorescent substance. In addition, the present invention relates to a kit used in the sugar chain fluorescent labeling method of the present invention.

A method referred to as reductive amination is commonly used to label sugar chains with a fluorescent reagent. A fluorescent reagent having an amino group is added to a sugar chain sample, the amino group of the fluorescent reagent is reacted with an aldehyde group formed on the sugar chain reducing terminal, and a fluorescent label is introduced onto the reducing terminal of the sugar chain by reducing the Schiff base formed with a reducing agent.

In order to increase the efficiency of sugar chain labeling in the present invention, opportunities for reacting are increased by increasing the concentration of the fluorescent reagent for the purpose of further increasing the yield of fluorescent-labeled sugar chains.

More specifically, the present invention is as described below.

(Sugar Chain)

Although there are no particular limitations thereon, sugar chains used in the present invention may be biological products such as blood, body fluid or tissue extracts, or may be sugar chain compounds produced by chemical synthesis.

In addition, the sugar chain included in the present invention can be selected from sugar chains bound to any of a glycoamino acid, glycopeptide, glycoprotein, glycolipid, glycosaminoglycan, proteoglycan, glycosylphosphatidylinositol, peptidoglycan or lipopolysaccharide, or free sugar chains.

(Sugar Chain Labeling)

An example of a method used to label a sugar chain includes allowing an aromatic amine to act on the sugar chain followed by bonding the sugar chain to the aforementioned labeling compound by a reductive amination reaction.

Although there are no particular limitations on the labeling reagent used provided it is an aromatic amine, it is preferably selected from the group consisting of substances containing an amino group as indicated below.

Examples of these substances include 2-aminobenzamide, 2-aminobenzoic acid, 8-aminopyrene-1,3,6-trisulfonate, 8-aminonaphthalene-1,3,6-trisulfonate, 2-amino-9(1OH)-acridone, 5-aminofluorescein, dansyl ethylenediamine, 7-amino-4-methylcoumarine, 3-aminobenzoic acid, 7-amino-1-naphthol and 3-(acetylamino)-6-aminoacridine, while 2-aminobenzamide and 2-aminobenzoic acid are effective in consideration of their availability as reagents and convenience of the reaction. In addition, derivatives of these substances are also used preferably provided their function as a labeling reagent is maintained.

In the case of using 2-aminobenzamide or 2-aminobenzoic acid as aromatic amine, although it is used at 0.35 mol/L under ordinary conditions, by using at a concentration of 0.5 mol/L or more and preferably 1.4 mol/L or more, labeling efficiency can be improved. However, since it becomes difficult to remove aromatic amine not used in the reaction if the concentration exceeds 3 mol/L, the most preferable concentration is 1.4 mol/L to 3 mol/L.

In addition, with respect to the amount of liquid, in the case of using particles for the carrier used to capture sugar chains, although the amount of liquid is required to be of a degree that allows the particles to be immersed therein, such as 50 μL with respect to 5 mg of particles, labeling efficiency can be increased by increasing the amount of liquid to 100 μL equal to twice that amount. Although the amount of liquid may exceed 100 μL, since it becomes difficult to remove aromatic amine not used in the reaction, the amount of liquid is preferably adjusted to between 100 μL and 200 μL relative to 5 mg of particles.

(Labeling by Reductive Amination Method)

More specifically, in the case of labeling with 2-aminobenzamide, labeling is achieved by adding 100 μl of a solution obtained by dissolving 2-aminobenzamide to a concentration of 1.4 M and sodium cyanoborohydride to a concentration of 1 M in 30% acetic acid/dimethylsulfoxide (DMSO) to a reaction vessel containing a purified sugar chain, followed by reacting for 1 hour to 10 hours at 30° C. to 70° C.

(Sugar Chain Capturing Carrier)

Although sugar chains can be allowed to react in the liquid phase, use of a sugar chain capturing carrier explained below makes it possible to continuously purify and recover sugar chains and label the sugar chains with a fluorescent reagent.

(Sugar Chain Capturing Carrier)

The aforementioned sugar chain capturing carrier is a carrier having reactive primary amino groups on the surface thereof for capturing sugar chains, and preferably has oxylamino groups or hydrazide groups for the aforementioned primary amino groups. This is preferable because these groups are able to react and bond with a sugar chain reducing terminal in the form of an aldehyde group even in the absence of an enzyme or coupling reagent and the like.

The aforementioned sugar chain capturing carrier is preferably a particle having a structure represented by the following general formula of Chemical Formula 1:

[Chemical Formula 1]

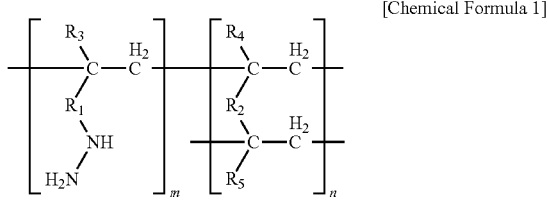

(in which, $R_1$ and $R_2$ represent hydrocarbon chains having 1 to 20 carbon atoms that may be inserted with —O—, —S—, —NH—, —CO— or —CONH—, $R_3$, $R_4$ and $R_5$ represent H, $CH_3$ or a hydrocarbon chain having 2 to 5 carbon atoms, and m and n represent the numbers of monomer units).

In addition, the aforementioned carrier is preferably a carrier that is insoluble in aqueous solution and organic solvent, and although there are no particular limitations on the material thereof, the material can be selected from among glass and resins having superior organic solvent resistance, such as silicon, polystyrene, ethylene-maleic anhydride copolymer or poly(methyl methacrylate).

The aforementioned carrier is preferably a particle having a polymer matrix having a crosslinked polymer structure represented by the following general formula of General Formula 2:

[Chemical Formula 2]

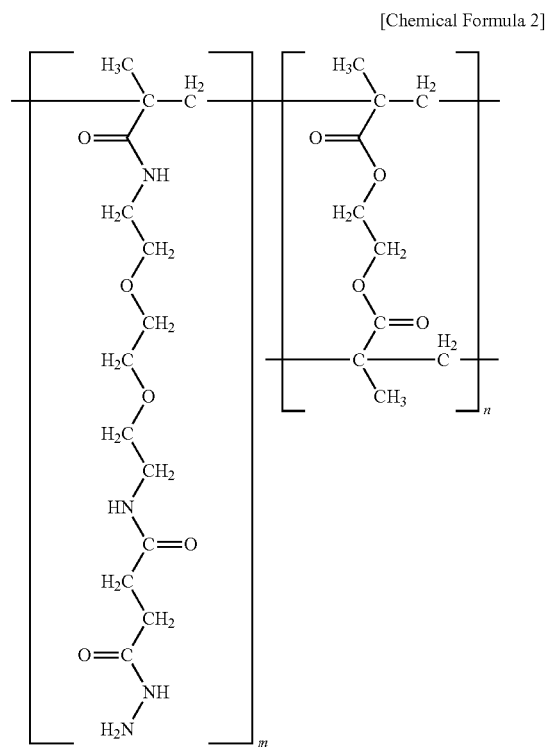

(in which, m and n are the same as previously defined).

Although there are no particular limitations thereon, the form of the aforementioned sugar chain capturing carrier is preferably in the form of a particle or plate. In order to produce a sugar chain library, a large number of samples must be processed simultaneously, and at that time, the use of a column packed with particles enables processing to be carried out continuously. In addition, the use of a multi-well plate also allows a large number of specimens to be processed simultaneously. A multi-well plate having 6, 12, 24, 48, 96 or 384 wells can be suitably used as a multi-well plate.

An inorganic substance can be used for the material of the particles except for the carrier of Chemical Formula 2. A particulate substance can be used for the inorganic substance that composes the aforementioned particles, and examples thereof include silica particles, alumina particles, glass particles and metal particles. In addition, polysaccharide gels represented by agarose and sepharose and polymers of vinyl compounds in particulate form can be used as organic polymer substances.

In addition, the shape of the particles is preferably spherical, and the average particle diameter thereof is preferably 0.1 μm to 500 μm. Average particle diameter in this case is determined by measuring the diameter of each particle observed in the field of view of a light microscope. Carrier particles having a particle diameter within this range are easily recovered by centrifugal separation or filtration and the like, and since they also have adequate surface area, they are considered to demonstrate high reaction efficiency with sugar chains. In the case particle diameter far exceeds the aforementioned range, reaction efficiency with sugar chains may decrease due to a reduction in surface area. In addition, in the case particle diameter is far below the aforementioned range, it may become difficult to recover the particles particularly by filtration. Moreover, in the case of using the particles by packing into a column, pressure loss during passage of liquid through the column may become large if particle diameter is excessively small.

In the present invention, there are no particular limitations on sugar chains immobilized on the carrier, and they may be biological products such as blood, body fluid or tissue extracts, or may be sugar chain compounds produced by chemical synthesis.

In addition, the sugar chain included in the present invention is selected from free sugar chains or sugar chains bound to any of a glycoamino acid, glycopeptide, glycoprotein, glycolipid, glycosaminoglycan, proteoglycan, glycosylphosphatidylinositol, peptidoglycan or lipopolysaccharide.

(Sugar Chain Capturing)

A specific example of the conditions of the bonding reaction between a sugar chain reducing terminal and primary amino group that uses the aforementioned sugar chain capturing carrier includes pH of 2 to 7, reaction temperature of 50° C. to 100° C., preferably 60° C. to 90° C. and more preferably 70° C. to 85° C., and reaction time of 15 minutes to 120 minutes. The most preferable conditions are pH of 3 to 6, reaction temperature of 80° C. and reaction time of 1 hour.

In the case pH is below 3 or higher than 7, capturing efficiency decreases since an intermediate in the form of an imine form is formed slowly. In the case the reaction temperature is below 50° C., reaction efficiency may become quite poor and sugar chains are unable to be adequately captured. The reaction is preferably carried out in an open system to completely evaporate solvent. This is for the purpose of allowing the reaction to proceed adequately as a result of the solvent concentration being infinitely concentrated as it evaporates.

In addition, in the case the reaction temperature exceeds 90° C., in addition to having a detrimental effect on the sugar chain per se, in the case the carrier is made of plastic, the carrier may be deformed or melted depending on the type thereof.

In the case the reaction time is shorter than 30 minutes, an adequate bonding reaction may be unable to be obtained, thereby preventing adequate capture of sugar chains. In addition, in the case the reaction time exceeds 90 minutes, there is no additional capturing of sugar chains, and only additional time is spent without demonstrating any effects.

(Removal of Contaminants)

After having captured a sugar chain, the sugar chain capturing carrier must be washed in order to remove contaminants.

Here, an alcohol such as methanol or ethanol, water, or an aqueous buffer and the like is used as the solution used for the washing solution. Here, in the case an aqueous solution is used for washing, the pH of the aqueous solution is preferably in the vicinity of neutral, and is preferably 4 to 10 and more preferably 6 to 8.

The carrier that has captured a sugar chain can be easily removed of contaminants other than the sugar chain in the purified raw material by washing, thereby enabling only the sugar chain to be recovered while still immobilized on the carrier.

In the case of particles, the particles can be washed using a washing method including immersing the particles in a washing solution and repeatedly changing the washing solution.

More specifically, after placing the particles in a centrifuge tube or other type of tube, adding washing solution and shaking, the particles are washed by repeating a procedure including precipitating the particles by centrifugation and removing the supernatant.

For example, after placing the particles in a centrifuge tube and adding washing solution, the particles can be washed by repeating a procedure including allowing the particles to settle spontaneously or forcibly depositing the particles by centrifugal separation and removing the supernatant. The aforementioned washing procedure is preferably repeated 3 to 6 times.

In the case of a plate, the plate can be easily washed by repeatedly dispensing washing solution into each well and then removing the washing solution by aspiration. In addition, the plate may also be washed as necessary using a centrifugal separator capable of centrifuging plates.

In addition, a filter tube in the form of a tubular container can also be used by installing a filter in the bottom thereof that has a pore diameter that allows the passage of liquid but does not allow the passage of the aforementioned particles. By using the aforementioned filter tube so that the particles are added therein, washing solution required for washing can be removed through the filter, thereby improving workability by eliminating the need for the aforementioned supernatant removal step following the centrifugation procedure.

In addition, various types of multi-well plates having 6 to 384 wells equipped with the aforementioned filter in the bottom thereof are commercially available, and the use of these plates enables processing at high throughput. In particular, a solution dispenser, aspiration removal system and plate transport system (such as the Biomek series available from Beckman Coulter Inc.) have been developed for 96-well plates and are optimum for high throughput, and a series of procedures may be carried out using this automated system.

In addition, in the case of using a multi-plate, substances other than the captured sugar chains may be removed by a filtration procedure or centrifugal separation.

Processing from the sugar chain capturing reaction to labeling may be carried out continuously in a column by packing a column with the sugar chain capturing carrier. As a result, a large volume of sugar chains can be purified and labeled.

EXAMPLES

Although the following provides a detailed explanation of the present invention based on examples and comparative examples, the present invention is not limited thereto.

Example 1

Preparation of Sugar Chain Sample

After dissolving 1 mg of IgG from bovine serum (Sigma Corp., 15506) in 50 μL of 100 mM ammonium bicarbonate (Wako Pure Chemical Industries, Ltd., 017-02875), 5 μL of 120 mM dithiothreitol (DTT, Sigma Corp., D9779) were added and allowed to react for 30 minutes at 60° C. Following completion of the reaction, 10 μL of 123 mM iodoacetoamide (IAA, Wako Pure Chemical Industries, Ltd., 093-02152) were added and allowed to react for 1 hour at room temperature while protecting from light. Continuing, the protein portion was fragmented into peptides by subjecting to protease treatment with 400 U of trypsin (Sigma Corp., T0303). After treating the reaction solution for 5 minutes at 90° C., treatment with 5 U of glucosidase F (Roche Diagnostics, 1-365-193) was carried out to release the sugar chain from peptide and obtain a pretreated biological sample.

(Sugar Chain Purification by Sugar Chain Capturing Carrier)

20 µL of the aforementioned sugar chain solution and 180 µL of 2% acetic acid/acetonitrile solution were added to a disposable column containing 5 mg of sugar chain capturing carrier in the form of particles having a hydrazide group (BlotGlyco®, Sumitomo Bakelite Co., Ltd., BS-45603) and allowed to react for 1 hour at 80° C. The reaction was carried out in an open system and the particles were visually confirmed to be in a dry state after completely evaporating off the solvent. After washing the particles with a guanidine solution, water, methanol and triethylamine solution, 10% acetic anhydride/methanol was added followed by allowing to react for 30 minutes at room temperature to cap unreacted hydrazide groups. After capping, the particles were washed with methanol, aqueous hydrochloric acid solution and water.

Continuing, 20 µL of ultrapure water and 180 µl of 2% acetic acid/acetonitrile solution were added to the disposable column containing the particles and allowed to react for 1.5 hours at 70° C. The reaction was carried out in an open system and the particles were visually confirmed to be in a dry state after completely evaporating off the solvent.

(Sugar Chain Labeling)

Labeling was carried out with 2-aminobenzamide (2-AB, Wako Pure Chemical Industries, Ltd., 574-92441). 100 µL of a solution prepared by dissolving 2-AB and sodium cyanoborohydride in a mixed solvent of 30% acetic acid and dimethylsulfoxide (DMSO) to a final concentration of 0.7 M and 1 M, respectively, were added to the disposable column containing the particles followed by allowing to react for 2 hours at 60° C.

(Removal of Excess 2-AB)

After recovering 50 µL of the reaction solution and diluting 10-fold with acetonitrile, the diluted reaction solution was added to a silica column (provided with the BlotGlyco Kit) to adsorb the labeled sugar chain onto silica gel. After washing the column with acetonitrile, the labeled sugar chain was recovered with 50 µL of ultrapure water.

(Detection of Labeled Sugar Chain)

The resulting labeled sugar chain was measured by HPLC. Measurement was carried out using an amino column (Shodex Asahipak NH2P-50) at an excitation wavelength of 330 nm and emission wavelength of 420 nm.

Example 2

With the exception of the sugar chain labeling step described below, preparation of the sugar chain sample, sugar chain purification by the sugar chain capturing carrier, removal of excess 2-AB and detection of the labeled sugar chain were carried out in the same manner as Example 1.

(Sugar Chain Labeling)

Labeling was carried out with 2-aminobenzamide (2-AB, Wako Pure Chemical Industries, Ltd., 574-92441). 100 µL of a solution prepared by dissolving 2-AB and sodium cyanoborohydride in a mixed solvent of 30% acetic acid and dimethylsulfoxide (DMSO) to a final concentration of 1.4 M and 1 M, respectively, were added to the disposable column containing the particles followed by allowing to react for 2 hours at 60° C.

Example 3

With the exception of the sugar chain labeling step described below, preparation of the sugar chain sample, sugar chain purification by the sugar chain capturing carrier, removal of excess 2-AB and detection of the labeled sugar chain were carried out in the same manner as Example 1.

(Sugar Chain Labeling)

Labeling was carried out with 2-aminobenzamide (2-AB, Wako Pure Chemical Industries, Ltd., 574-92441). 100 µL of a solution prepared by dissolving 2-AB and sodium cyanoborohydride in a mixed solvent of 30% acetic acid and dimethylsulfoxide (DMSO) to a final concentration of 2.8 M and 1 M, respectively, were added to the disposable column containing the particles followed by allowing to react for 2 hours at 60° C.

Example 4

With the exception of the sugar chain labeling step described below, preparation of the sugar chain sample, sugar chain purification by the sugar chain capturing carrier, removal of excess 2-AB and detection of the labeled sugar chain were carried out in the same manner as Example 1.

(Sugar Chain Labeling)

Labeling was carried out with 2-aminobenzamide (2-AB, Wako Pure Chemical Industries, Ltd., 574-92441). 200 µL of a solution prepared by dissolving 2-AB and sodium cyanoborohydride in a mixed solvent of 30% acetic acid and dimethylsulfoxide (DMSO) to a final concentration of 1.4 M and 1 M, respectively, were added to the disposable column containing the particles followed by allowing to react for 2 hours at 60° C.

Comparative Example 1

With the exception of the sugar chain labeling step described below, preparation of the sugar chain sample, sugar chain purification by the sugar chain capturing carrier, removal of excess 2-AB and detection of the labeled sugar chain were carried out in the same manner as Example 1.

(Sugar Chain Labeling)

Labeling was carried out with 2-aminobenzamide (2-AB, Wako Pure Chemical Industries, Ltd., 574-92441). 100 µL of a solution prepared by dissolving 2-AB and sodium cyanoborohydride in a mixed solvent of 30% acetic acid and dimethylsulfoxide (DMSO) to a final concentration of 0.35 M and 1 M, respectively, were added to the disposable column containing the particles followed by allowing to react for 2 hours at 60° C.

Comparative Example 2

With the exception of the sugar chain labeling step described below, preparation of the sugar chain sample, sugar chain purification by the sugar chain capturing carrier, removal of excess 2-AB and detection of the labeled sugar chain were carried out in the same manner as Example 1.

(Sugar Chain Labeling)

Labeling was carried out with 2-aminobenzamide (2-AB, Wako Pure Chemical Industries, Ltd., 574-92441). 50 µL of a solution prepared by dissolving 2-AB and sodium cyanoborohydride in a mixed solvent of 30% acetic acid and dimethylsulfoxide (DMSO) to a final concentration of 1.4 M and 1 M, respectively, were added to the disposable column containing the particles followed by allowing to react for 2 hours at 60° C.

Figure 2:
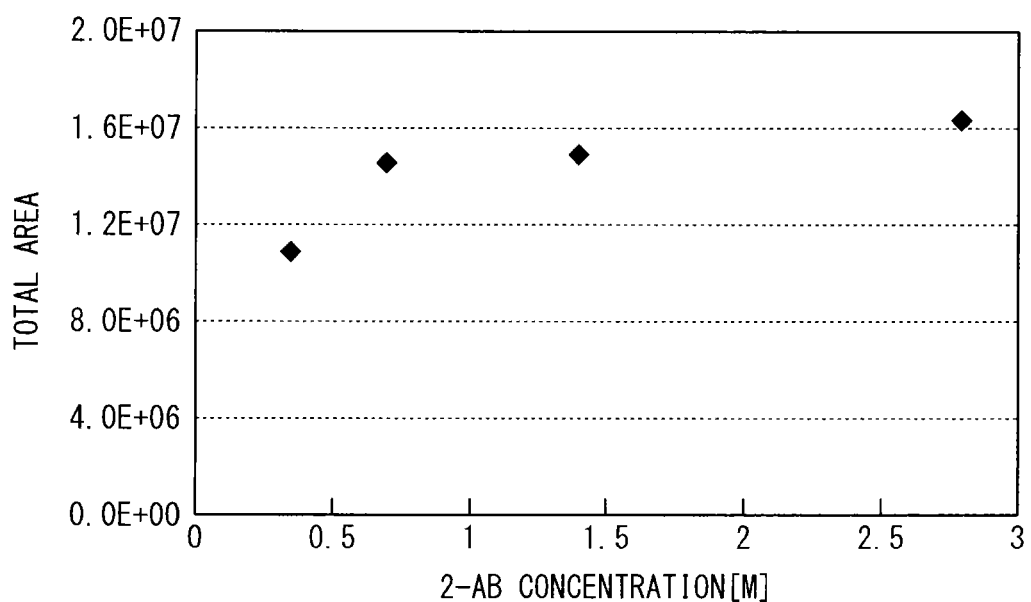
FIG. 2 is a graph of the total areas of peaks obtained in Examples 1, 2 and 3 and Comparative Example 1 of the present application.

A typical example of an HPLC chart obtained in the aforementioned study is shown in FIG. 1. In addition, a graph of the total areas of the peaks obtained in Examples 1, 2 and 3 and Comparative Example 1 is shown in FIG. 2. The total areas of the resulting peaks increased as the concentration increased beyond the commonly used concentration of 0.35 M.

Figure 3:
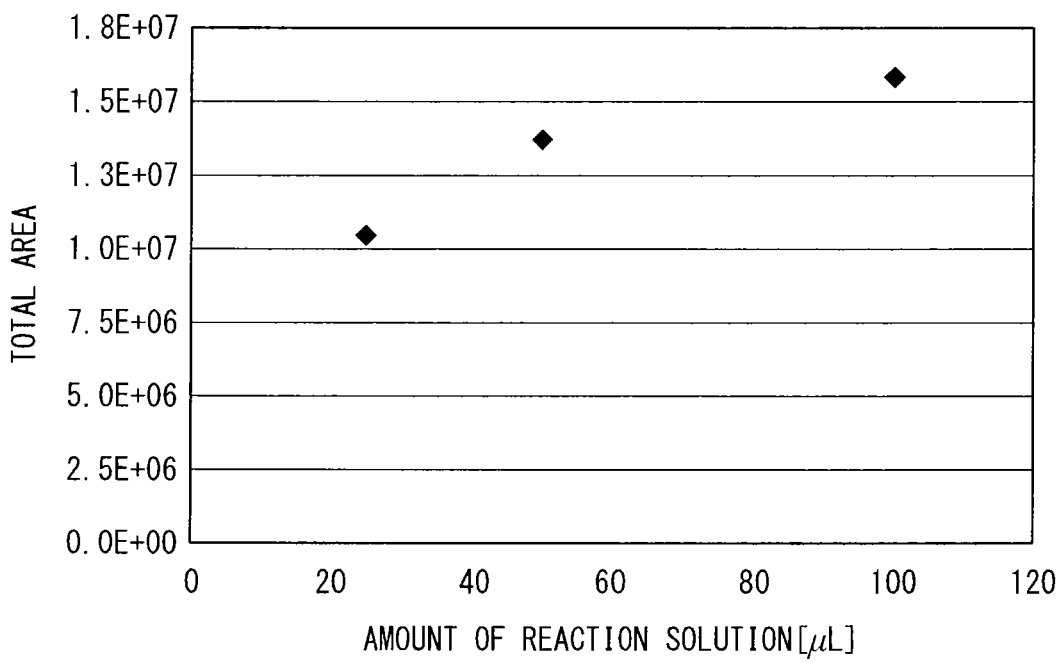
FIG. 3 is a graph of the total areas of peaks obtained in Examples 2 and 4 and Comparative Example 2 of the present application.

Continuing, a graph of the total areas of the peaks obtained in Examples 2 and 4 and Comparative Example 2 is shown in FIG. 3. The total areas of the resulting peaks increased as the amount of solution increased beyond 50 µL.

On the basis of the aforementioned results, the sugar chain fluorescent labeling method of the present application, which including capturing and purifying a sugar chain using a sugar chain capturing carrier, releasing the sugar chain and labeling the free sugar chain with a high concentration (0.5 mol/L or more) of a fluorescent substance including an aromatic amine, clearly demonstrated superior effects.

INDUSTRIAL APPLICABILITY

According to the present invention, a sugar chain can be easily recovered and purified, and sugar chain labeling can be carried out with an aromatic amine to provide the aforementioned sugar chain.

The invention claimed is:

1. A sugar chain fluorescent labeling method, comprising:
   reacting a sugar chain with 2 aminobenzamide at a concentration of from 0.7 mol/L to 3 mol/L such that the sugar chain is labeled with 2 aminobenzamide.

2. The sugar chain fluorescent labeling method according to claim 1, wherein the sugar chain is captured with a sugar chain capturing carrier, a captured sugar chain is released from the sugar chain capturing carrier such that a free sugar chain is obtained, and the free sugar chain is reacted with 2 aminobenzamide.

3. The sugar chain fluorescent labeling method according to claim 2, wherein the sugar chain capturing carrier is a polymer particle having a structure of Chemical Formula 1:

[Chemical Formula 1]

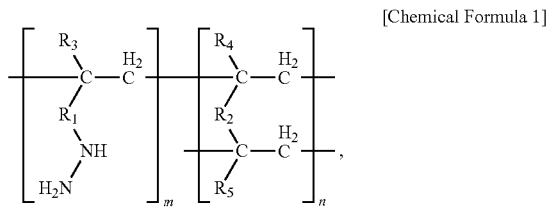

wherein, $R_1$ and $R_2$ are each independently a hydrocarbon chain having 1 to 20 carbon atoms that may be inserted with —O—, —S—, —NH—, —CO— or —CONH—, $R_3$, $R_4$ and $R_5$ are each independently a H, $CH_3$ or a hydrocarbon chain having 2 to 5 carbon atoms, and m and n are each independently a number of monomer units.

4. The sugar chain fluorescent labeling method according to claim 2, wherein the sugar chain capturing carrier is a polymer particle having a structure of following Chemical Formula 2:

[Chemical Formula 2]

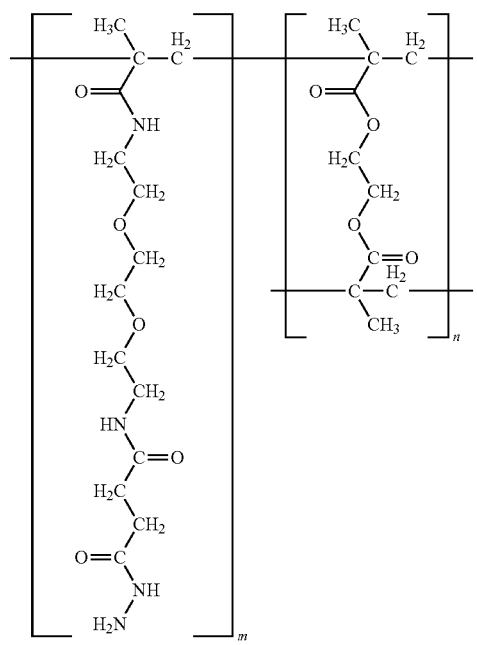

wherein, m and n are each independently a number of monomer units.

5. The sugar chain fluorescent labeling method according to claim 1, wherein the sugar chain is a biological product.

6. The sugar chain fluorescent labeling method according to claim 1, wherein the sugar chain is a sugar chain bound to a glycoamino acid, glycopeptide, glycoprotein, glycolipid, glycosaminoglycan, proteoglycan, glycosylphosphatidylinositol, peptidoglycan, or lipopolysaccharide, or a free sugar chain.

7. The sugar chain fluorescent labeling method according to claim 1, wherein 2 aminobenzamide is reacted at a concentration of from 1.4 mol/L to 3 mol/L.

8. The sugar chain fluorescent labeling method according to claim 7, wherein the sugar chain is bound to a glycoamino acid, glycopeptide, glycoprotein, glycolipid, glycosaminoglycan, proteoglycan, glycosylphosphatidylinositol, peptidoglycan, or lipopolysaccharide.

9. The sugar chain fluorescent labeling method according to claim 7, wherein the sugar chain is captured with a sugar chain capturing carrier, a captured sugar chain is released from the sugar chain capturing carrier such that a free sugar chain is obtained, and the free sugar chain is reacted with 2 aminobenzamide.

10. The sugar chain fluorescent labeling method according to claim 9, wherein the sugar chain capturing carrier is a polymer particle having a structure of Chemical Formula 1:

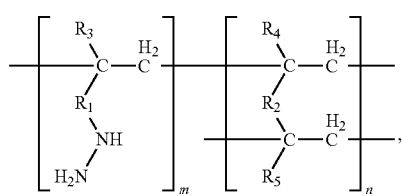

where $R_1$ and $R_2$ are each independently a hydrocarbon chain having 1 to 20 carbon atoms that may be inserted with —O—, —S—, —NH—, —CO— or —CONH—, $R_3$, $R_4$ and $R_5$ are each independently a H, $CH_3$ or a hydrocarbon chain having 2 to 5 carbon atoms, and m and n are each independently a number of monomer units.

11. The sugar chain fluorescent labeling method according to claim 9, wherein the sugar chain capturing carrier is a polymer particle having a structure of following Chemical Formula 2:

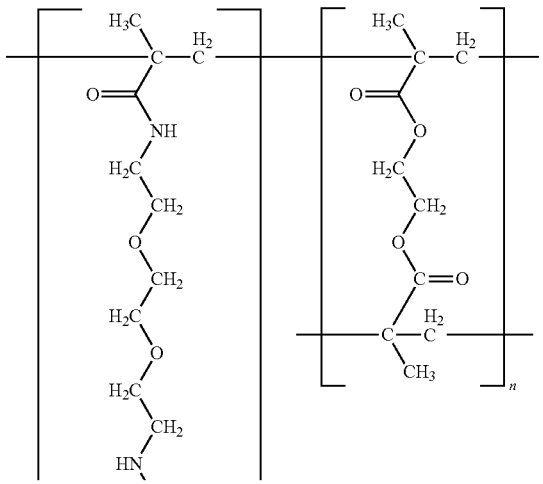

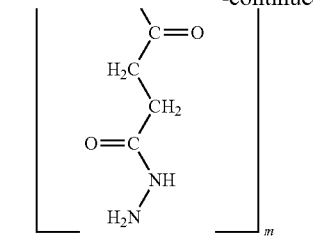

where m and n are each independently a number of monomer units.

12. The sugar chain fluorescent labeling method according to claim 1, wherein 2-aminobenzamide is reacted at a concentration of from 0.7 mol/L to 1.4 mol/L.

13. The sugar chain fluorescent labeling method according to claim 1, wherein 2-aminobenzamide is reacted at 0.7 mol/L.

14. The sugar chain fluorescent labeling method according to claim 1, wherein 2-aminobenzamide is reacted at 1.4 mol/L.

* * * * *